United States Patent [19]

Hults et al.

[11] Patent Number: 4,671,793
[45] Date of Patent: Jun. 9, 1987

[54] DISPOSABLE TRAINING PANTS

[76] Inventors: Rhondalee R. Hults; George Spector, both of 233 Broadway RM 3615, New York, N.Y. 10007

[21] Appl. No.: 768,156

[22] Filed: Aug. 22, 1985

[51] Int. Cl.⁴ .............................................. A61F 13/16
[52] U.S. Cl. .................................. 604/385 R; 604/394; 604/391
[58] Field of Search .................. 604/385.1, 358, 359, 604/394, 393, 389, 391, 392, 397, 398, 399

[56] References Cited

U.S. PATENT DOCUMENTS

| | | | |
|---|---|---|---|
| 2,575,163 | 11/1951 | Donovan | 604/394 |
| 3,039,466 | 6/1962 | Wilson | 604/394 |
| 3,658,064 | 4/1972 | Pociluyko | 604/385 A |
| 3,828,785 | 8/1974 | Gamm et al. | 604/394 |
| 3,882,871 | 5/1975 | Taniguchi | 604/385 A |
| 3,926,189 | 12/1975 | Taylor | 604/359 |
| 4,576,601 | 3/1986 | Brain | 604/398 |
| 4,615,695 | 10/1986 | Cooper | 604/394 X |
| 4,617,022 | 10/1986 | Pigneul et al. | 604/391 |

*Primary Examiner*—John D. Yasko

[57] ABSTRACT

Disposable training pants for a young child is provided and consists of a one piece configuration to be worn by children of an age between one to two years old. The training pants has a plastic outer cover and an inner absorbent lining being thin at the sides and thick in the middle crotch area from front to back. In a modified form the inner absorbent lining is removable from the plastic outer cover so as to be replaceable when needed.

2 Claims, 4 Drawing Figures

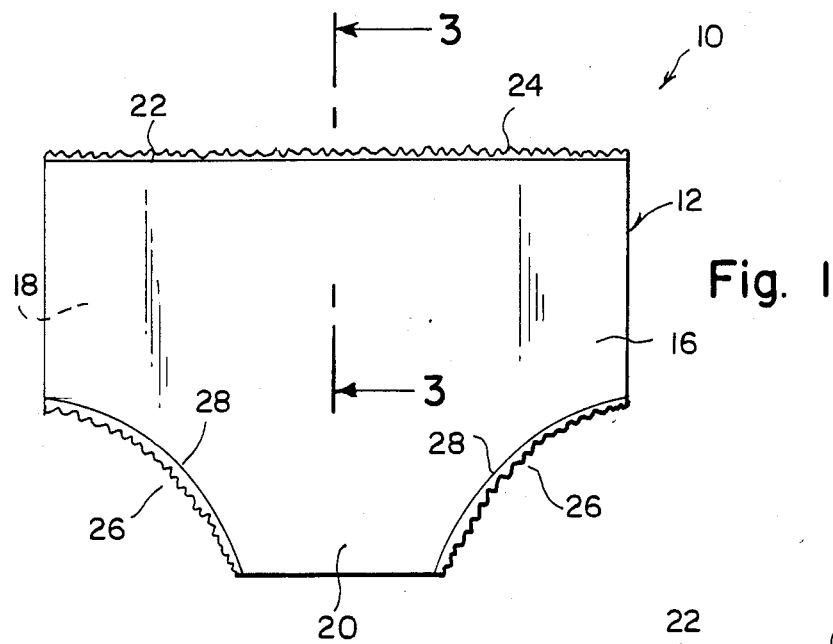
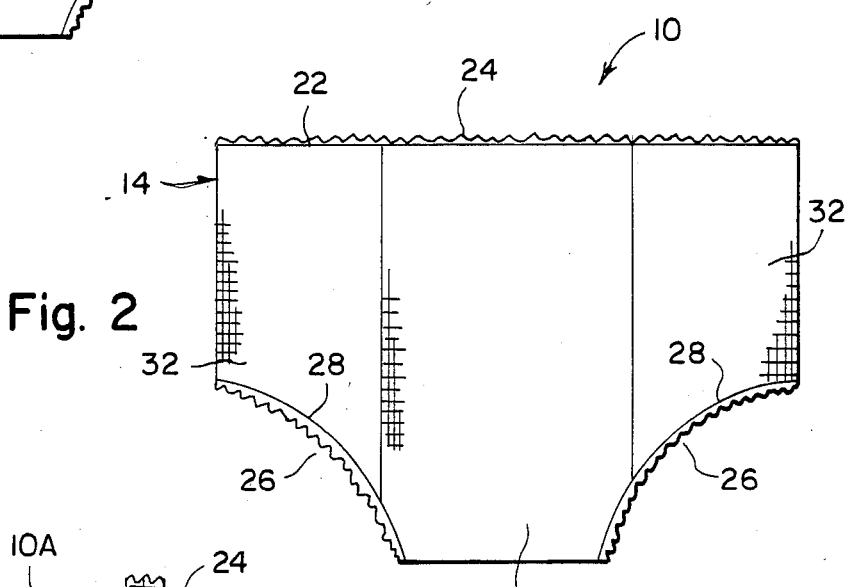
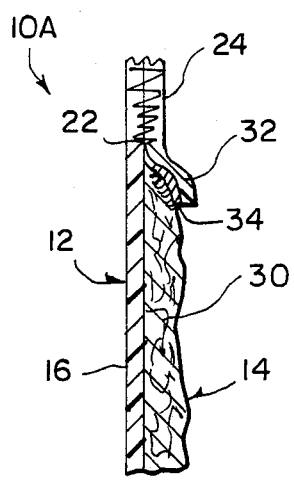

DISPOSABLE TRAINING PANTS

BACKGROUND OF THE INVENTION

The instant invention relates generally to absorbent underpants and more specifically it relates to a disposable training pants.

Numerous absorbent underpants have been provided in prior art that are adapted to keep garments of the wearer free from moisture. For example, U.S. Pat. Nos. 1,329,119; 3,756,878 and 4,427,408 all are illustrative of such prior art. While these units may be suitable for the particular purpose to which they address, they would not be as suitable for the purpose of the present invention as heretofore described.

SUMMARY OF THE INVENTION

A principle object of the present invention is to provide disposable training pants that is of a one piece configuration to be worn by children of an age between one to two years old.

Another object is to provide a disposable training pants that has a plastic outer cover and an inner absorbent lining being thin at the sides and thick in the middle crotch area from front to back.

An additional object is to provide disposable training pants wherein the inner absorbent lining is removable from the plastic outer cover so as to be replaceable when needed.

A further object is to provide disposable training pants that is economical in cost to manufacture.

A still further object is to provide disposable training pants that is simple and easy to use.

Further objects of the invention will appear as the description proceeds.

To the accomplishment of the above and related objects, this invention may be embodied in the form illustrated in the accompanying drawings, attening being called to the fact, however, that the drawings are illustrative only, and that changes may be made in the specific construction illustrated and described within the scope of the appended claims.

BRIEF DESCRIPTION OF THE DRAWING FIGURES

FIG. 1 is an exterior elevational view of the invention showing the plastic outer cover of the disposable training pants.

FIG. 2 is an interior elevational view of the invention showing the inner absorbent lining having thin absorbent padding at the sides with the absorbent thick padding in the middle crotch area from front to back of the disposable training pants.

FIG. 3 is an enlarged cross sectional view taken along line 3—3 in FIG. 1.

FIG. 4 is an enlarged cross sectional view similar to FIG. 3 of a modification showing interior absorbent lining being removable from the exterior plastic coating thus making just the inner absorbent lining disposable.

DETAILED DESCRIPTION OF THE PREFERRED EMBODIMENTS

Turning now descriptively to the drawings, in which similar reference characters denote similar elements throughout the several views, FIGS. 1 through 3 illustrates disposable training pants 10 for a young child (not shown). The training pants 10 consists of an outer cover 12 of waterproof material and an inner absorbent lining 14.

The outer cover 12 includes front and back portions 16 and 18 with an intermediate crotch area 20. The top edges 22 of the front and back portions are a waistband 24 for the cover 12. The crotch area 20 has leg openings 26 at side edges 28.

The inner absorbent lining 14 is thicker at the crotch area from the front to back as indicated by numeral 30. The other portions 32 of lining 14 are of a thinner layer. The lining 14 is suspended from the waistband 24 of the cover 12.

The waistband 24 and the side edges 28 of the leg openings 26 are of elastic material such as rubber or the like, that makes the training pants 10 form fitting on the young child so as to reduce moisture leakage therefrom.

The waterproof material of the outer cover 12 is plastic while the inner absorbent lining 14 is fabricated out of paper padding.

In FIG. 4 a modified training pants 10A is shown. An inner VELCRO strip 32 is affixed to the waistband 24 of the cover 12. The VELCRO strip 32 will make contact with upper edge 34 of the inner absorbent lining 14. The lining can now be removably suspended from the waistband 24, of the cover 12 so as to be replaceable when needed.

While certain novel features of this invention have been shown and described and are pointed out in the annexed claims, it will be understood that various omissions, substitutions and changes in the forms and details of the device illustrated and in its operation can be made by those skilled in the art without departing from the spirit of the invention.

What is claimed is:

1. Disposable training pants for a young child which comprises:
   (a) an outer cover of waterproof material including front and back portions with an intermediate crotch area with top edges of said front and back portions being a waistband for said cover and said crotch area having leg openings at side edges thereof; and
   (b) a full inner absorbent lining of similar configuration as said cover, being thicker at said crotch area from said front to back, said lining suspended from said waistband of said cover and thinner at the outer portions adjacent the waistband, wherein said waistband and said side edges of said leg openings are of elastic material to be form fitting for said young child so as to reduce moisture leakage therefrom, further comprising an inner VELCRO strip adfixed to said waistband of said cover said strip being mounted on a flap depending from said waistband so that said VELCRO strip will overlap and contact over the upper edge of said inner absorbent lining so that said lining can now be conveniently and sealingly removeably suspended from said waistband of said cover so as to be replaceable when needed.

2. Disposable training pants for a young child which comprises:
   (a) an outer cover of waterproof material including front and back portions with an intermediate crotch area with top edges of said front and back portions being a waistband for said cover and said crotch area having leg openings at side edges thereof; and (b) a full inner absorbent circumferential lining of similar configuration as said cover, being thicker at said crotch area from said front to back, said lining suspended from said waistband of said cover and thinner at a circumferential upper edge adjacent the waistband, wherein said waistband and said side edges of said leg openings are of elastic material to be form fitting for said young child so as to reduce moisture leakage therefrom, further comprising an inner VELCRO strip circumferentially affixed to said waistband of said cover said strip being mounted on a circumferential flap depending from said waistband so that said VELCRO strip will overlap and contact over said upper edge of said inner absorbent lining so that said lining can now be conveniently and sealingly removeably suspended from said waistband of said cover so as to be replaceable when needed.

* * * * *